(12) United States Patent
Chmura et al.

(10) Patent No.: US 11,986,670 B2
(45) Date of Patent: May 21, 2024

(54) SYSTEM AND METHOD FOR MULTI-SITE RADIOTHERAPY

(71) Applicant: THE UNIVERSITY OF CHICAGO, Chicago, IL (US)

(72) Inventors: Steven J Chmura, Chicago, IL (US); Shan Lu, Chicago, IL (US); Ralph R. Weichselbaum, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 644 days.

(21) Appl. No.: 17/274,908

(22) PCT Filed: Sep. 18, 2019

(86) PCT No.: PCT/US2019/051710
§ 371 (c)(1),
(2) Date: Mar. 10, 2021

(87) PCT Pub. No.: WO2020/061179
PCT Pub. Date: Mar. 26, 2020

(65) Prior Publication Data
US 2022/0047892 A1 Feb. 17, 2022

Related U.S. Application Data

(60) Provisional application No. 62/733,263, filed on Sep. 19, 2018.

(51) Int. Cl.
*A61N 5/10* (2006.01)
(52) U.S. Cl.
CPC ........... *A61N 5/103* (2013.01); *A61N 5/1077* (2013.01)

(58) Field of Classification Search
CPC ........ A61N 5/103; A61N 5/1077; A61N 5/00; A61N 5/01; A61N 5/10; A61N 5/1038
See application file for complete search history.

(56) References Cited

U.S. PATENT DOCUMENTS

| 2010/0183121 A1 | 7/2010 | Riker et al. |
| 2012/0136194 A1 | 5/2012 | Zhang et al. |
| (Continued) |

FOREIGN PATENT DOCUMENTS

WO  2017156316 A1  9/2017

OTHER PUBLICATIONS

International Search Report and Written Opinion for PCT Application PCT/US2019/051710, mailed Dec. 4, 2019, 15 pages.

*Primary Examiner* — Christine S. Kim
(74) *Attorney, Agent, or Firm* — Armstrong Teasdale LLP

(57) ABSTRACT

A method of radiating a plurality of masses in a patient is provided, including receiving a three-dimensional model of the patient, the model including respective locations of a plurality of OARs, receiving a set of locations in the model corresponding to the masses, respective prescribed radiation dosages for the masses, and respective radiation limits for the OARs. The method includes computing a candidate set of beams having respective beam paths that travel through at least one of the masses. The method includes scoring the candidate set of beams based on respective dosages provided to the masses, respective dosages provided to the OARs, and beams in a set of selected beams for treatment, adding a best-scoring beam among the candidate set of beams to the set of selected beams, and radiating the masses using the set of selected beams.

23 Claims, 10 Drawing Sheets

(56) References Cited

U.S. PATENT DOCUMENTS

| | | | |
|---|---|---|---|
| 2016/0016008 A1* | 1/2016 | Kelly | A61N 5/103 600/1 |
| 2017/0354832 A1 | 12/2017 | Bush et al. | |
| 2018/0043184 A1* | 2/2018 | Wu | A61N 5/1077 |
| 2022/0047892 A1* | 2/2022 | Chmura | A61N 5/103 |
| 2022/0161058 A1* | 5/2022 | Peltola | A61N 5/1075 |

* cited by examiner

SYSTEM AND METHOD FOR MULTI-SITE RADIOTHERAPY

CROSS-REFERENCE TO RELATED APPLICATIONS

This application is a U.S. National Phase Application of PCT/US2019/051710, filed Sep. 18, 2019, which claims priority to U.S. Provisional Patent Application No. 62/733,263 titled "System and Method for Multi-Site Radiotherapy," filed on Sep. 19, 2018 by University of Chicago, the entire contents of which are hereby incorporated herein by reference.

FIELD

The field of the invention relates generally to planning and administering radiotherapy to patients having one or more tumors or other masses and, more particularly, to a system and method of radiating multiple masses in a patient in a single radiotherapy session.

BACKGROUND

The goal of radiotherapy is to maximize the probability of tumor cure while minimizing normal tissue damage. Radiotherapy generally has been concerned with local tumor control as an alternative to surgery or use with surgery and/or chemotherapy to improve local control. Recently radiotherapy has been employed in the potential cure of metastatic disease.

Over the past 3 decades, radiotherapy has evolved from radiation delivery techniques using bony anatomy and hand-drawn blocking toward specialized planning incorporating three-dimensional reconstructions of images and computer optimization algorithms. Modern radiation planning involves a dosimetrist or physicist to initially determine radiation beam angles and initial shape of the target. Subsequently the treatment planning systems (such as those made by Varian, Phillips, etc.) further refine the output of the machine-modulated radiation dose. Despite the capability of planning and calculating doses accurately to within millimeters to a single target, little attention has been paid to treating multiple targets at a time while avoiding the critical Organs at Risk (OAR). Until recently, there has not been a clinical need for treating multiple areas in the body with high-dose radiotherapy. The need now exists to plan multiple metastases simultaneously with the increased integration of radiotherapy, specifically Stereotactic Body Radio Therapy (SBRT or SABR) to augment systemic (chemotherapy, immunotherapy, and other targeted therapy) treatment of metastatic disease. In addition, improving the speed to treat multiple sites in the body would also increase the speed of treating even a single site.

Recent studies with high dose radiotherapy demonstrate an improvement in both progression-free survival and overall survival (OS) of metastatic patients who have a few metastases (oligometastases). There is now a desire to extend this paradigm to integrate with targeted agents and immunotherapies in this era of personalized medicine. These treatments require many hours to plan given the inherent human inefficiency with choosing angles for one metastases, let alone multiple ones. Thus, most treatments have been limited to 1-2 metastases with a minority of patients being treated for 3-4 metastases (see NRG Oncology BR001 NCT02206334). A system is needed to extend this paradigm to more metastases.

This Background section is intended to introduce the reader to various aspects of art that may be related to the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

One aspect is directed to a method of radiating a plurality of masses in a patient. The method includes receiving a three-dimensional model of the patient, the three-dimensional model including respective locations of a plurality of organs at risk. The method includes receiving a set of locations in the three-dimensional model corresponding to the plurality of masses. The method includes receiving respective prescribed radiation dosages for the plurality of masses. The method includes receiving respective radiation limits for the plurality of organs at risk. The method includes computing a candidate set of beams having respective beam paths that travel through at least one of the plurality of masses. The method includes scoring the candidate set of beams based on respective dosages provided to the plurality of masses, respective dosages provided to the plurality of organs at risk, and beams in a set of selected beams for treatment. The method includes adding a best-scoring beam among the candidate set of beams to the set of selected beams. The method includes radiating the plurality of masses using the set of selected beams.

Another aspect is directed to a system for administering radiation therapy for a plurality of masses in a patient. The system includes a radiation therapy beam generator and an interface configured to receive a three-dimensional model of the patient including respective locations of a plurality of organs at risk, a set of locations in the three-dimensional model corresponding to the plurality of masses, respective prescribed radiation dosages for the plurality of masses, and respective radiation limits for the plurality of organs at risk. The system includes a processing system coupled to the interface and the radiation therapy beam generator. The processing system is configured to compute a candidate set of beams having respective beam paths that travel through at least one of the plurality of masses. The processing system is configured to score the candidate set of beams based on respective dosages provided to the plurality of masses, respective dosages provided to the plurality of organs at risk, and beams in a set of selected beams for treatment. The processing system is configured to add a best-scoring beam among the candidate set of beams to the set of selected beams. The processing system is configured to transmit the set of selected beams to the radiation therapy beam generator. The processing system is configured to initiate generation of the set of selected beams by the radiation therapy beam generator.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

Although specific features of various embodiments may be shown in some drawings and not in others, this is for convenience only. Any feature of any drawing may be referenced and/or claimed in combination with any feature of any other drawing.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

Embodiments of the systems and methods described herein provide a set of algorithms that select initial beam angles to treat an unlimited number of tumors by focusing on minimizing a number of beams and passing those beams through as many tumors as possible to minimize dose to normal organs (OAR) and maximize the dose to the tumors. The system then sends the beam angle data to the treatment planning system that calculates the final beamlets and modulation.

In at least some embodiments, given a set of tumors, or masses, the systems and methods described herein assume a sphere of beams around the patient as candidates, subtracting those that are not practical or useful (e.g., beams that do not pass any tumor). The system then scores and ranks all the candidate beams based on each beam's ability to cover tumors and their impact on normal organs, while automatically excluding those that would make the treatment less safe based on known parameters. The system then automatically picks the top ranked beams that collectively provide the desired dosage to all or any sub-set of tumors while minimizing the impact on normal organs. The systems and methods may be utilized by a physician who can customize and adjust the scoring function by specifying a desired dosage for each tumor and a sensitivity of normal organs through a human computer interface. Such an interface may include using a color coding or moving sliders around. The physician may elect to treat all or any number of metastases.

Figure 1:
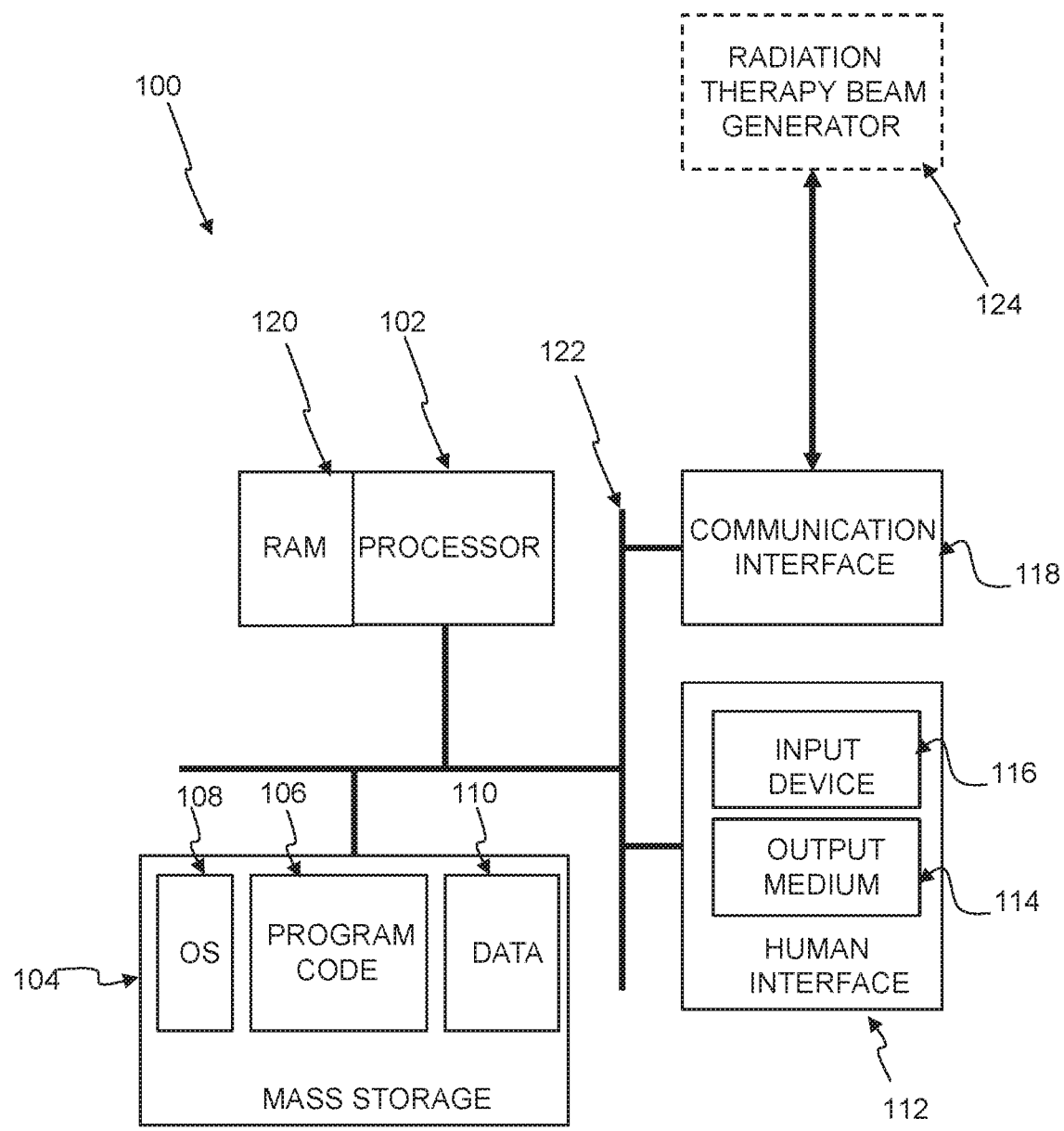
FIG. 1 is a block diagram of an example computing system.

FIG. 1 is a block diagram of an example computing system 100. Computing system 100 may include a mobile computing device, a desktop computing system, a server, or any other suitable computing platform. Computing system 100 includes a processor 102 for executing instructions and a mass storage 104, or memory. In some implementations, executable instructions, or program code 106, are stored in mass storage 104. Mass storage 104 may also include allocations for storing an operating system 108 or data 110. Processor 102 includes one or more processing units (e.g., in a multi-core configuration). Mass storage 104 may include processor-executable instructions enabling use of a human interface 112 and a communication interface 118. Mass storage includes, but is not limited to, any computer-operated hardware suitable for storing and/or retrieving computer-executable instructions and/or data. For example, mass storage 104 is any device that enables information such as program code 106 or data 110 to be stored and retrieved. Mass storage 104 may include one or more computer-readable storage devices or other non-volatile computer readable media. For example, mass storage 104 may include multiple storage units such as hard disks or solid state disks in a redundant array of inexpensive disks (RAID) configuration. Mass storage 104 may include a storage area network (SAN) and/or a network attached storage (NAS) system. In some implementations, mass storage 104 includes memory that is integrated into computing system 100. For example, computing system 100 may include one or more hard disk drives as mass storage 104. Mass storage 104 may also include memory that is external to computing system 100 and may be additionally accessible by one or more other computing systems. The above memory types are exemplary only, and are thus not limiting as to the types of memory usable for storage of processor-executable instructions and/or data.

Computing system 100 includes human interface 112 having one or more output medium 114 for presenting information to a user. Output medium 114 may include any component capable of conveying information to the user, such as, for example, a video adapter operatively couplable to an output device such as a display device (e.g., a liquid crystal display (LCD), organic light emitting diode (OLED) display, cathode ray tube (CRT), or "electronic ink" display), or an audio adapter operatively couplable to an audio output device (e.g., a speaker or headphones). In some embodiments, at least one such display device and/or audio device is included in output medium 114.

Human interface 112 includes an input device 116 for receiving input from the user. Input device 116 may include, for example, a keyboard, a keypad, a pointing device, a mouse, a stylus, a touch sensitive panel (e.g., a touch pad or a touch screen), a gyroscope, an accelerometer, a position detector, or an audio input device. A single component such as a touch screen may function as both an output device of output medium 114 and input device 116.

Computing system 100 also includes communication interface 118 that is communicatively couplable to a remote computing device, such as a radio therapy beam generator 124, over a communication channel, such as, for example, Ethernet. Communication interface 118 includes, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Computing system 100 includes random access memory (RAM) 120. RAM 120 may include one or more memory devices such as dynamic RAM (DRAM) or static RAM (SRAM). Additionally, computing system 100 may include one or more other units of memory, including, for example, read-only memory (ROM), erasable programmable read-only memory (EPROM), electrically erasable programmable read-only memory (EEPROM), and non-volatile RAM (NVRAM). RAM 120 may be integrated with processor 102, implemented as a separate device from processor 102, or both.

Computing system 100 includes a data bus 122 that enables communication and transfer of data among processor 102, RAM 120, mass storage 104, communication interface 118, and human interface 112. Data bus 122 may further provide for communication and transfer of data with one or more other peripheral computing devices, input devices, output devices, additional memory, or any other device with which computing system may interface. Data bus 122 may include, for example, one or more buses utilizing standards such as ISA, PCI, AGP, SCSI, SATA, eSATA, IEEE 1394, Infiniband, USB, Firewire, or any other suitable parallel or serial communication and transfer of data within and/or external to computing system 100.

Figure 2:
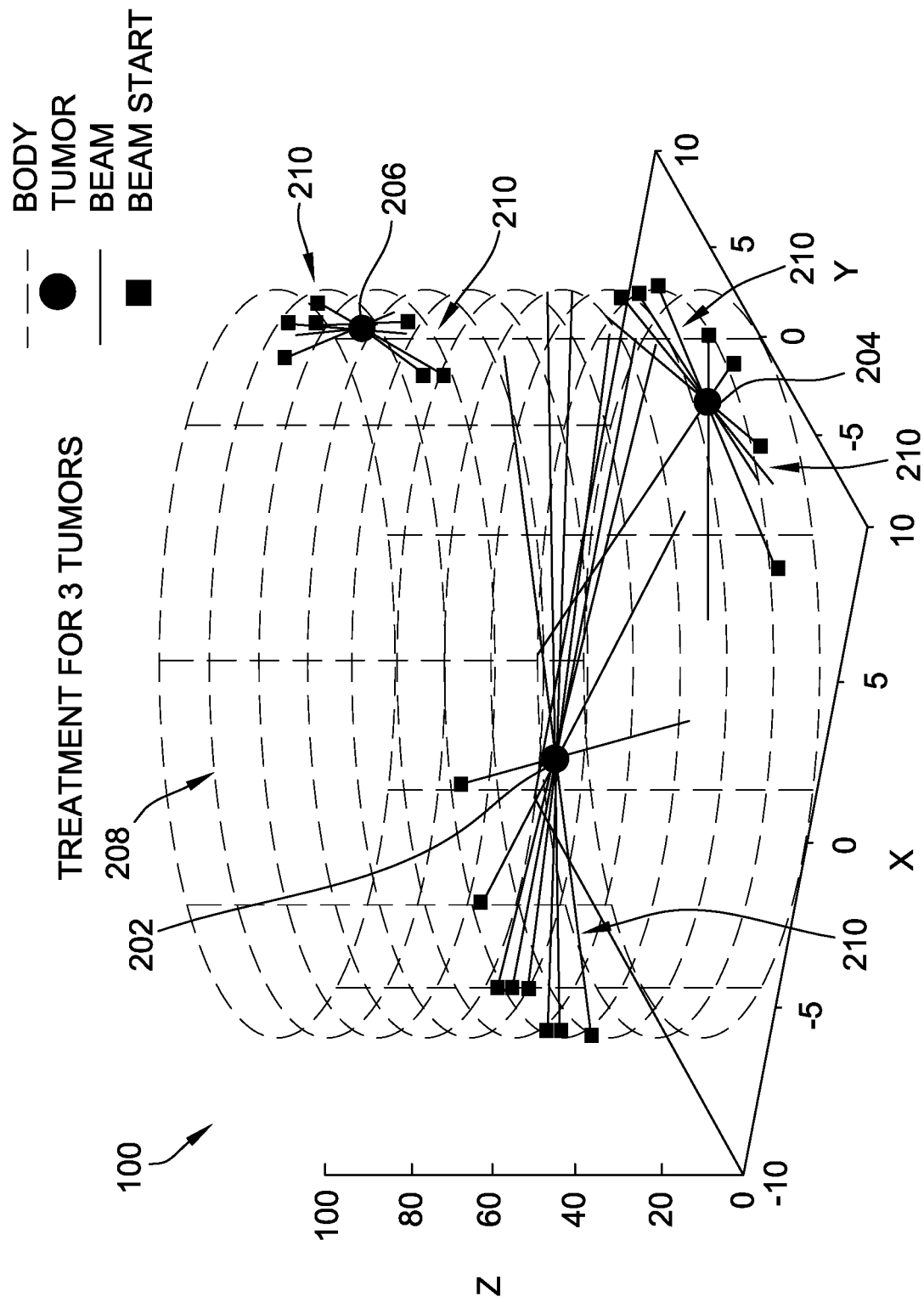
FIG. 2 is a diagram of an example treatment plan.
Figure 3:
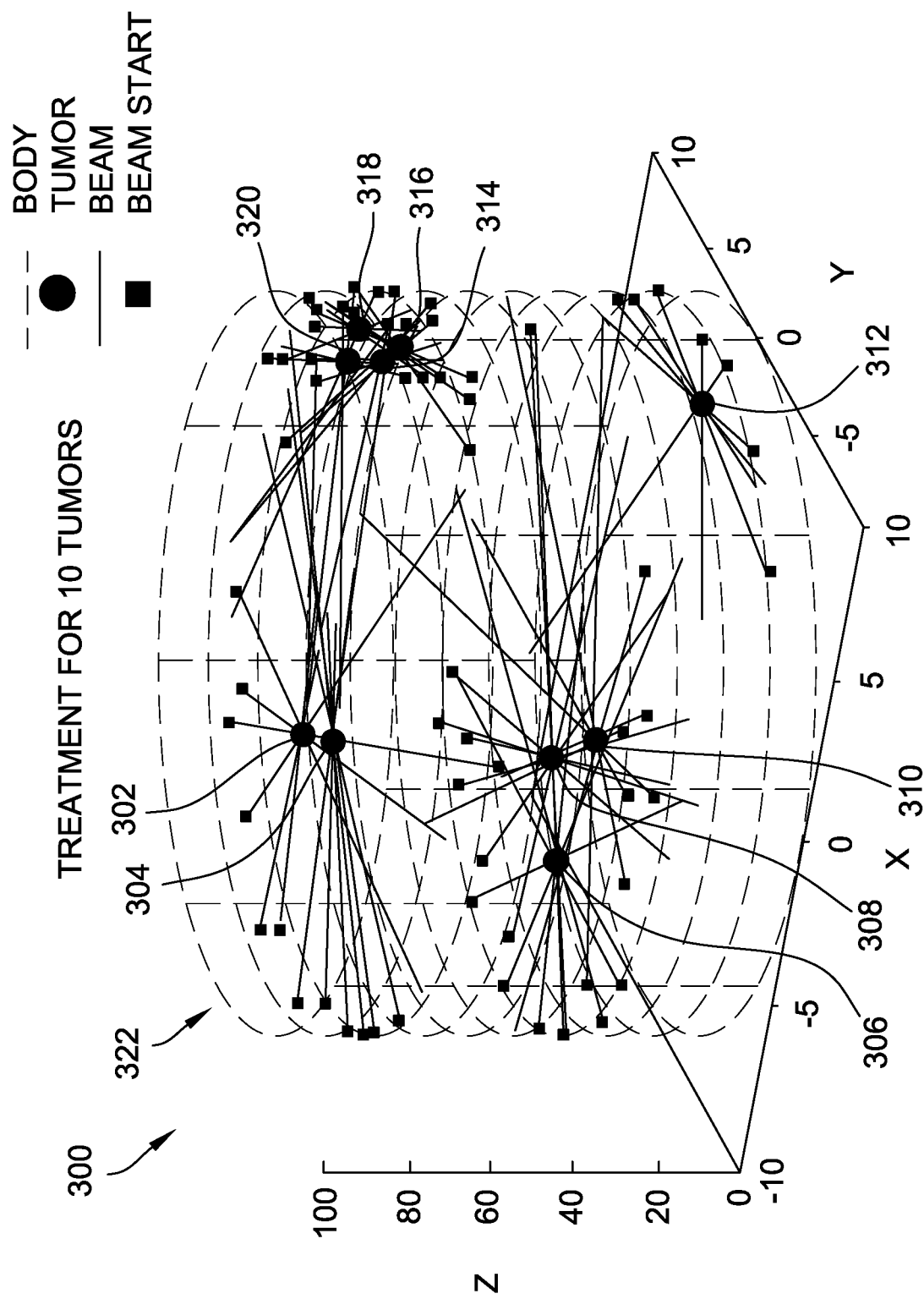
FIG. 3 is a diagram of another example treatment plan.

FIG. 2 is a diagram of an example treatment plan 200 for three tumors 202, 204, 206 within a patient 208. FIG. 3 is a diagram of another example treatment plan 300 for ten tumors 302, 304, 306, 308, 310, 312, 314, 316, 318, 320 within a patient 322. FIGS. 2 and 3 illustrate treatment plans 200 and 300 generated by systems and methods described herein. Treatment plans 200 and 300 provide each tumor five to six times more dosage than any normal organs, i.e., OAR. In the examples shown in FIGS. 2 and 3 model patients' human body as a 20 cm×20 cm×100 cm cylinder, and each tumor is modeled as a 1 cm-diameter ball. When the tumors are far away from each other, like tumors 202, 204, 206 shown in FIG. 2, they are each treated by different beams, which are represented by vectors 210 drawn from respective beam starting points, represented by square markers, and through tumors 202, 204, 206. When the tumors are near each other, like tumors 314, 316, 318, 320 shown in FIG. 3, two tumors could be covered by one beam in the treatment plan, where each beam is represented by vectors 324 drawn from respective beam starting points, represented by square markers, and through tumors 302, 304, 306, 308, 310, 312, 314, 316, 318, 320. The beams start from the side of the body that is closer to a tumor. For a tumor that is close to skin, like tumors 204 and 206 shown in FIG. 2, the treatment, i.e., the beams, only touches a small part of the body. Conversely, for a tumor that is near the center of the body, like tumor 202 shown in FIG. 2, the treatment needs to touch more areas of the body. Conventionally, treatment plans would be generated manually by an expert physician over a long period of time. Treatment plans 200 and 300 are automatically generated by systems and methods described herein in less than a second.

As radiotherapy expands from focusing on treating one organ with small doses spread over many weeks to use as a systemic therapy in this era of precision medicine, improved efficiency is needed to test whether improvements in progression-free survival (PFS) and overall survival (OS) can be seen. Without sophisticated computer-based initial setup, it is simply not practical—and in many cases impossible—for humans to complete this task.

In one embodiment, a treatment plan is generated using an algorithm implemented at least partially on a computing system, such as computing system 100 shown in FIG. 1. The algorithm receives inputs including, for example:

(1) a 3-dimensional human-body model M, including a set of Organs at Risk (OAR=$\{o_1, o_2, \ldots, o_m\}$) (this is reconstructed from a CT scan of a patient under treatment);

(2) the locations of all k tumors to be treated T=$\{t_1, t_2, \ldots t_k\}$ inside the body; and (3) the radiation dosage prescribed by the doctor to each tumor DT=$\{dt_1, dt_2, \ldots dt_k\}$, $dt_i$ is the desired minimum dosage for tumor $t_i$; and the dosage constraint for each organ at risk DO=$\{do_1, do_2, \ldots do_m\}$, $do_j$ is the desired maximum dosage for an organ $o_j$.

The output of this algorithm is a set of beams B that will be used to treat all of the tumors T during radiation therapy, for example, using radio therapy beam generator 124 shown in FIG. 1. These selected beams are referred to as treatment beams.

The system ensures every target tumor t gets at least the prescribed radiation dosage, but not much more than that; and ensures every organ at risk gets dosage not much more than the prescribed dosage constraint. The system does not aim to find the absolutely optimal treatment beam set, which is extremely time consuming and mostly unnecessary in practice, and instead aims to find a very good set of treatment beams quickly. In practice, there is a large number of candidates for treatment beams—entering the human body at any point with any angle—and there are exponential number of beam subsets for the algorithm to choose from. Finding the absolutely optimal treatment beam set is an NP-hard problem, and is unlikely to be accomplished within a reasonable amount of time and with a reasonable amount of computational resources.

Figure 4:
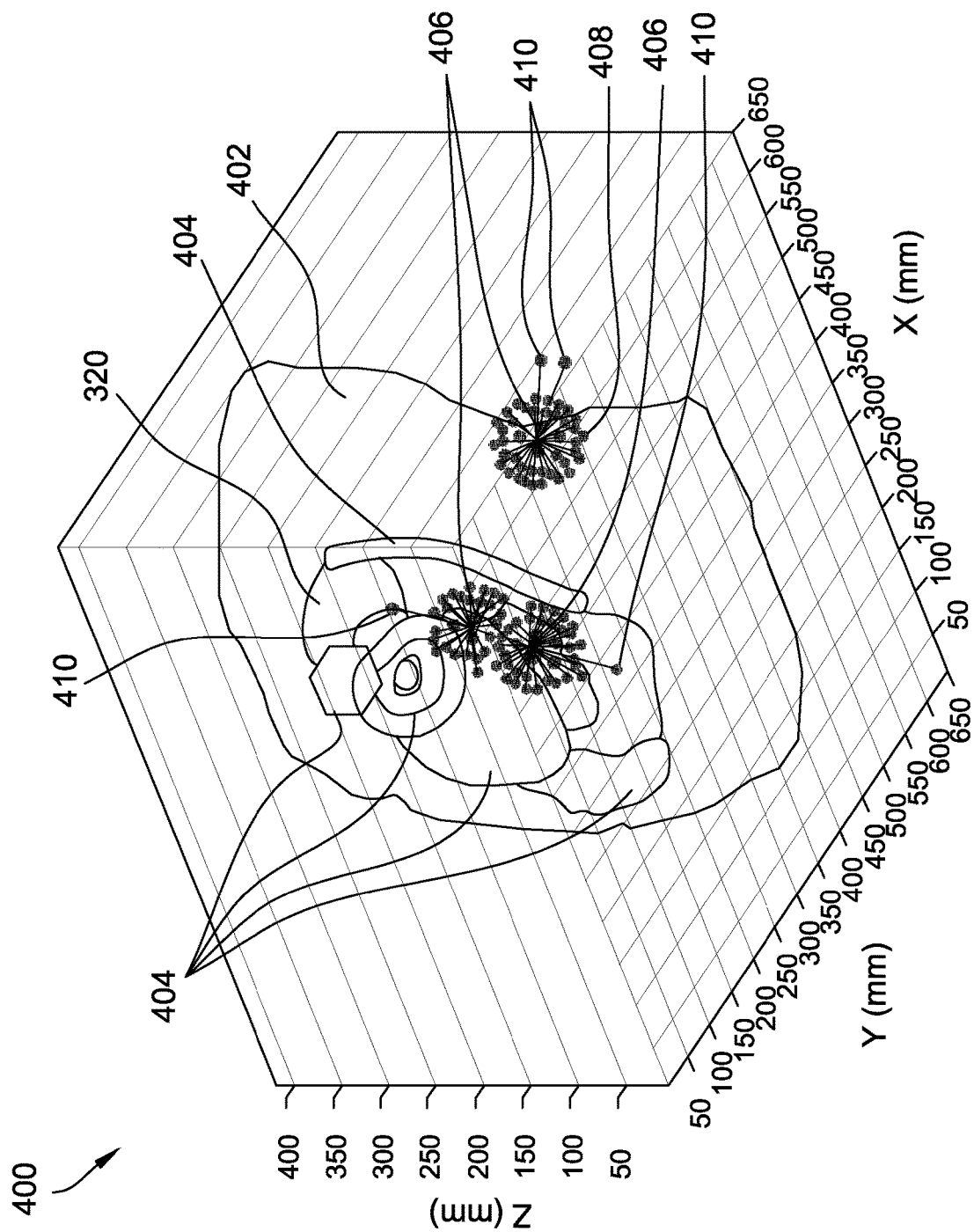
FIG. 4 is a graphical illustration of a patient.

FIG. 4 is a graphical illustration 400 of a patient for which a treatment plan is being generated by the systems and methods described herein. FIG. 4 includes a model of the patient 402 and various OARs 404. The model of patient 402 is reconstructed from a CT scan. The model of patient 402 also includes several tumors 406, each surrounded by numerous beam starting points 408, shown by circle markers with vectors drawn through tumors 406 representing the candidate beams.

Table 1 below is an example of pseudo-code for use generally in the systems and methods described herein.

TABLE 1

PSEUDO CODE SAMPLE 1

```
1   TreatementSet = empty;
2   CandidateSet = GetCandidates (M, T); // Step-I, M is the human
    body model, T are tumors
3   treated = 0; //recording how many tumors have reached prescribed
    dosage
4   while (treated< sizeof(T)) { // exit once all tumors got prescribed
    dosage
5     if (NeedtoUpdateScores( )){
6       for every beam b_i in CandidateSet – TreatementSet
7         score [i] = GetScore (b_i, T, OAR);
8     }
9     pickOneBeam (CandidateSet, TreatementSet, &pickedBeam,
        &treated);
10    if (pickedBeam == -1) break; //no available candidate
11    TreatementSet.add (pickedBeam); //add to treatment beam set
```

With reference to FIG. 4, the system first trims down the candidate space. Not all beams in the 3-dimensional space are useful for treating tumors 406. Beams that do not go through any tumors 406, or only go through a tumor 406 when the radiation energy has decreased to 0 are clearly not practical for treatment, and should be eliminated from the candidate set. These beams are excluded by starting from the geometric center of every tumor 406 and sampling a fixed number of evenly distributed beams, or beam starting points 408, for each tumor 406. In alternative embodiments, the beams are excluded by starting from sampled locations on the skin of the patient, and selecting one beam for every pair of skin-location and tumor 406. These resulting beams enter the human body from the skin location and go through the geometric center of the tumor 406.

The resulting candidate beams would all provide positive radiation dosage to one or more tumors 406. Then, beams that go through at least two tumors are identified. To identify these beams, the system iterates through every pair of tumors 406 and computes beams 410 that connect the geometric centers of both tumors 406.

The number of beams the system generates in the candidate set is a tunable parameter. A user can choose to sample more intensely and get more candidate beams 408 going through each tumor 406. Likewise, they can also choose to have more beams 410 going through at least two tumors 406 by connecting other parts (e.g., not the geometric center) of every pair of tumors 406.

The system then scores every candidate beam based on how it contributes toward providing the desired dosage to tumors while minimizing dosage to other part of the body. Specifically, given a beam 408, 410, the system computes how much total dosage it leaves on all tumors 406 that it goes through and how much total dosage it leaves to the OARs. The scoring uses a ratio of these dosages (dose to tumor to dose to OAR) as a score for the beam. A higher score is indicates a beam is better than another in maximizing dose to the tumors 406 and minimizing the dose to OARs.

The scoring function for a beam generally reflects three aspects: (1) a beam should score higher if it provides dosage to a tumor; (2) a beam should score lower if it provides dosage to an organ at risk; and (3) the amount of increase or reduction for a beam should take into account what other beams have already been included in the treatment plan. For example, when a tumor 406 already receives close-to-target dosage from prior-selected beams, less scoring increase should be given to beams that go through this tumor. Likewise, when an organ already receives close-to-upper-bound dosage from prior-selected beams, more penalty should be given to beams that go through this organ.

In certain embodiments, an example scoring function includes, given a beam $b_i$, a tumor voxel j, and an organ voxel k, the score of this beam at a tumor voxel j is:

$$scoreT[i][j] = \frac{dose\ [i][j]}{dt[j]} * \min\left(1 - \frac{received\ [j]}{dt[j]}, 0\right)$$

where dt[j] is the prescribed dosage goal at tumor j, dose[i][j] is the dosage imposed by the beam i at the voxel j, and received[j] is the dosage already received by voxel j so far. The score of this beam at an organ voxel k is:

$$scoreO[i][k] = \begin{cases} \frac{dose\ [i][k]}{do[k]}, & \text{if received } [k] < do[k] \\ \frac{dose\ [i][k]}{do[k]} * \left(\frac{received\ [k]}{do[k]}\right)^2, & \text{if received } [k] \geq do[k] \end{cases}$$

where do[k] is the specified dosage upper-bound goal at organ voxel k, dose[i][k] is the dosage imposed by the beam i at the voxel k, and received [k] is the dosage already received by voxel k so far. The scores are combined for all tumor voxels and all organ voxels to get a total score for the beam i:

$$score\ [i] = \sum_j scoreT[i][j] - \sum_k scoreO[i][k]$$

In certain embodiments, there are multiple variations of the above scoring functions. For example, a different granularity of the scoring function may be utilized. In practice, different parts of a tumor (or organ) will receive different amount of dosage from a beam. Accordingly, the scoring function can be calculated with different granularity. The finest granularity would be per-voxel based, as the example above, and the coarsest granularity would be per-tumor/organ based. That is, instead of computing how much dosage is deposited on a tumor/organ voxel as shown above, the system computes how much dosage in total has been deposited on the whole tumor/organ and computes a score accordingly. Another alternative scoring method is to partition each tumor or organ into several parts, with each part consisting of multiple voxels, and then compute scores using each partition as a unit. Each alternative includes different trade-offs in terms of dosage optimization and computation cost.

In alternative embodiments, there could be different mathematical relationships (linear, quadratic, exponential, etc.) that follow the high-level scoring scheme above. For example, the system uses a quadratic in the computation of beam score above. In alternative embodiments, a score may be computed using a function with higher-order terms raised to a third power, fourth power, or other exponential. In further alternative embodiments, different organs could potentially take on different scoring functions. For example, for some organs, the total amount of dosage matters; for some other organs, like the spinal cord, not a single voxel can receive an over-the-limit dosage. Consequently, different mathematical operators can be used to accommodate for different medical needs. In other alternative embodiments, the scoring function may combine the impact to tumor and to organs linearly, e.g., by computing a difference between a tumor score and an OAR score.

Once beams are scored, the system picks treatment beams iteratively. The system evaluates all the candidate beams and picks the one that has a best, or highest, score. The system moves it from the candidate set to the treatment beam set. Once one beam is picked, the scores of all the remaining beams are updated. For example, once a tumor t has received the prescribed dosage from all the beams already selected, providing dosage to t no longer contributes to providing the prescribed dosage and should not be scored higher. The system iterates again picks the highest-scored beam from the remaining beams. The above process continues until the treatment dosage goal for every tumor D={d1, d2, . . . dk} is satisfied, or when the candidate set is empty. In alternative embodiments, treatment beams are re-scored less frequently to tune the optimization accuracy and the computation cost.

Once the treatment beams are selected, they can be directly used by physicians as treatment plans and for generating beams using radio therapy beam generator 124 (shown in FIG. 1), or they can serve as the initial plan from which additional manual or automated refinement may begin.

Table 2 below is another example of pseudo-code for use generally in the systems and methods described herein.

TABLE 2

PSEUDO CODE SAMPLE 2

```
1   TreatementSet = empty;
2   CandidateSet = CoverAtLeastOneTumor (M, T); //First Step, M is
    the human body model, T are tumors
3   for every beam bi in CandidateSet
4     score [i] = dosage (bi, T) / dosage (bi, M-T); // Use existing
      algorithm to compute dosage received
                                       // by tumors and non-
                                       tumors in body
5   treated = 0; //recording how many tumors have reached prescribed
    dosage
6   while (treated< sizeof(T)) { // exit once all tumors got prescribed
    dosage
7     max = 0;
8     max-index=0;
9     for every beam bi in CandidateSet
10      if (score [i] > max)
11        {max = score [i]; max-index=i;}
12    if (max == 0) break; //no available candidate
13    TreatementSet.add (max-index); //add to treatment beam set
14    score [max-index] = 0; //remove this beam from candidate set
15    now_treated = UpdateDosage(T); //update the dosage received
      by every tumor with this new
16                                 //addition of treatment beam; return number of
                                   tumors that are done
17    if (now_treated > treated) { //the new beam helps some tumors
      reach prescribed dose
18      UpdateScore (score, TreatementSet); //adjust scores
19      treated = now_treated;
20    }
21  }
```

In alternative embodiments, beams may also be removed from the candidate set for additional reasons and scoring functions may vary. For example, additional candidate beams may be removed based on knowledge of the radiation therapy machine and the human body (e.g., certain part of human body should never be used as places where a radiation beam enters body), etc. In another alternative embodiment, scoring may be customized by a physician. For example, in addition to considering the overall dosage received by all normal organs, doctors can specify certain extremely sensitive organs that should be protected from radiation more than other organs and the score function can add penalties for dosages left on these organs. Doctors can also specify different priorities of different tumors under treatment. The system enables different weights for dosages received by different tumors. In such embodiments, a higher weight results in more attention put on that organ or tumor. This weight is multiplied with a raw dosage score computed according to the scoring functions described above. These priority scores can be adjusted at any time, offering different treatment plan options to doctors in an interactive manner through the system's human interface.

In certain embodiments, once one beam is picked from the candidate set, it and its nearby beams are removed from the candidate set. A physician may also decide to end the treatment beam selection before the system iterates to its natural end.

In certain embodiments, more refinement may be applied to the result of the basic algorithm. For example, the resulting treatment beam set may be used as a seeding input to classic optimization algorithms like gradient descent algorithms or simulated annealing algorithms to determine if a better treatment plan is available that is similar to the plan generated by the systems and methods described herein. Generally, traditional optimization algorithms will function well given such a large initial search space. Accordingly, a good seed input may improve performance of these optimization algorithms. Alternatively, an intensity modularized treatment optimization algorithm may be applied to further define the exact density and shape of each selected beam.

Figure 5:
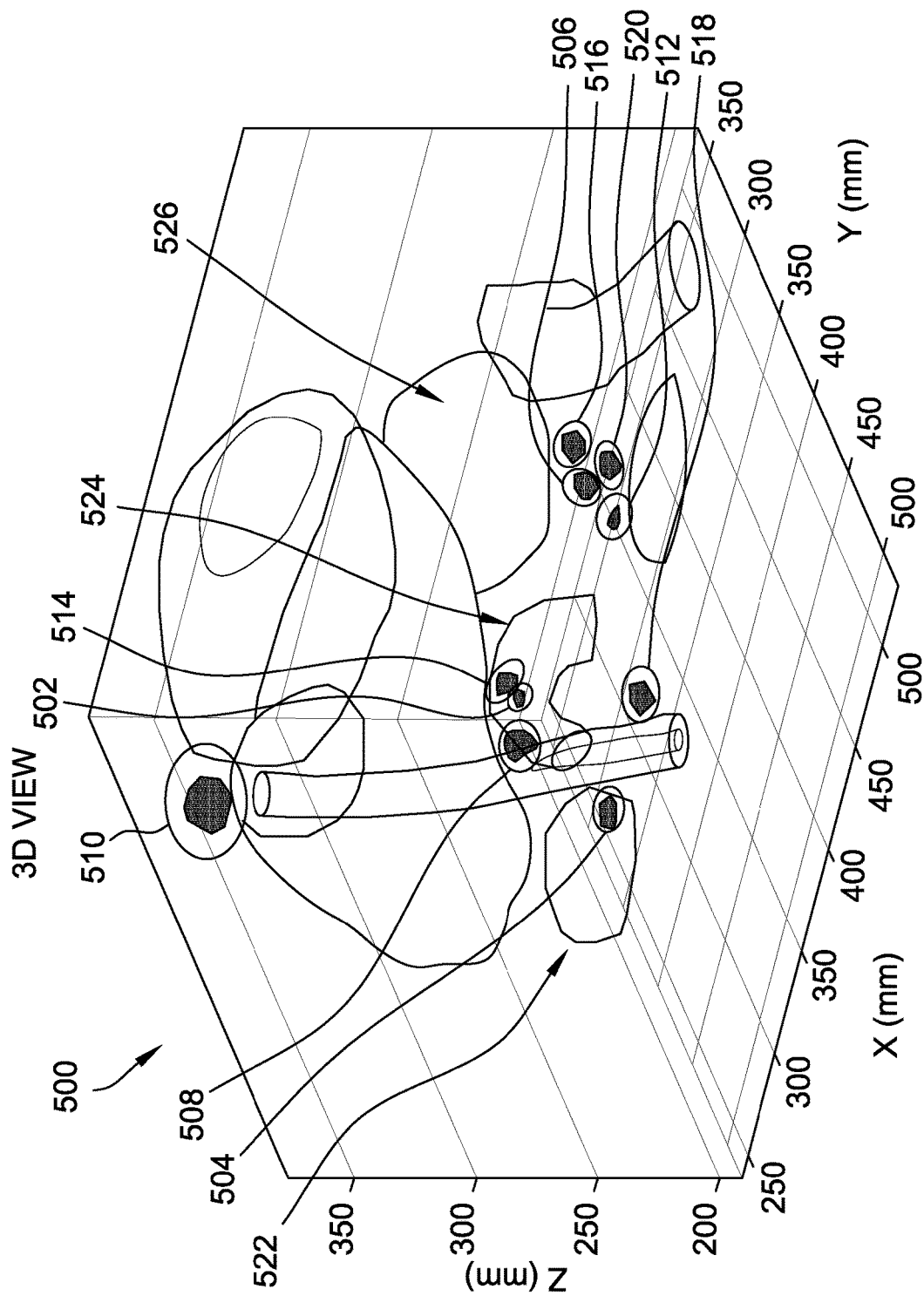
FIG. 5 is an overview of a patient model and ten tumors.
Figure 6:
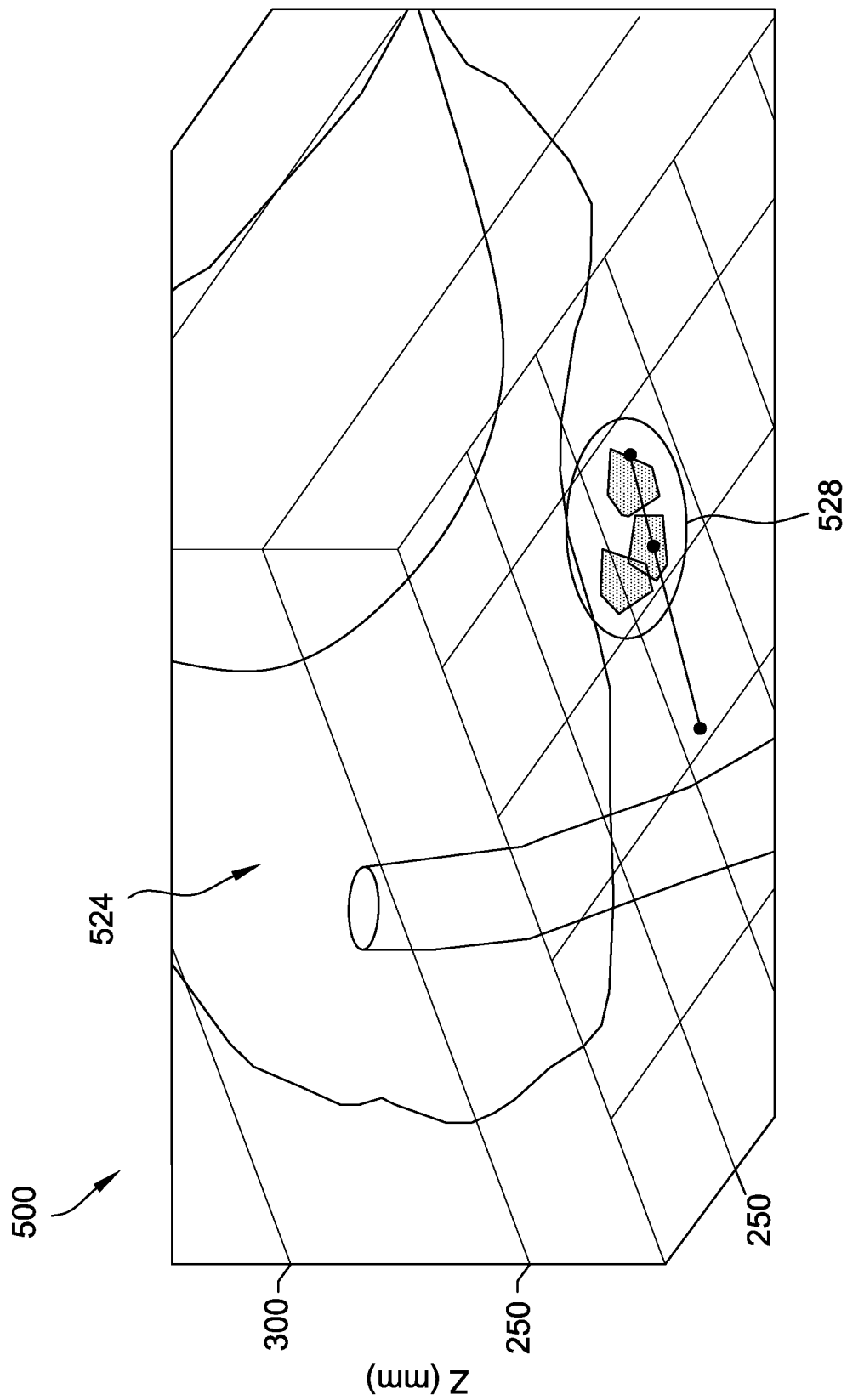
FIG. 6 is a detailed view of the liver in the patient model shown in FIG. 5 and a group of tumors collected beneath.
Figure 7:
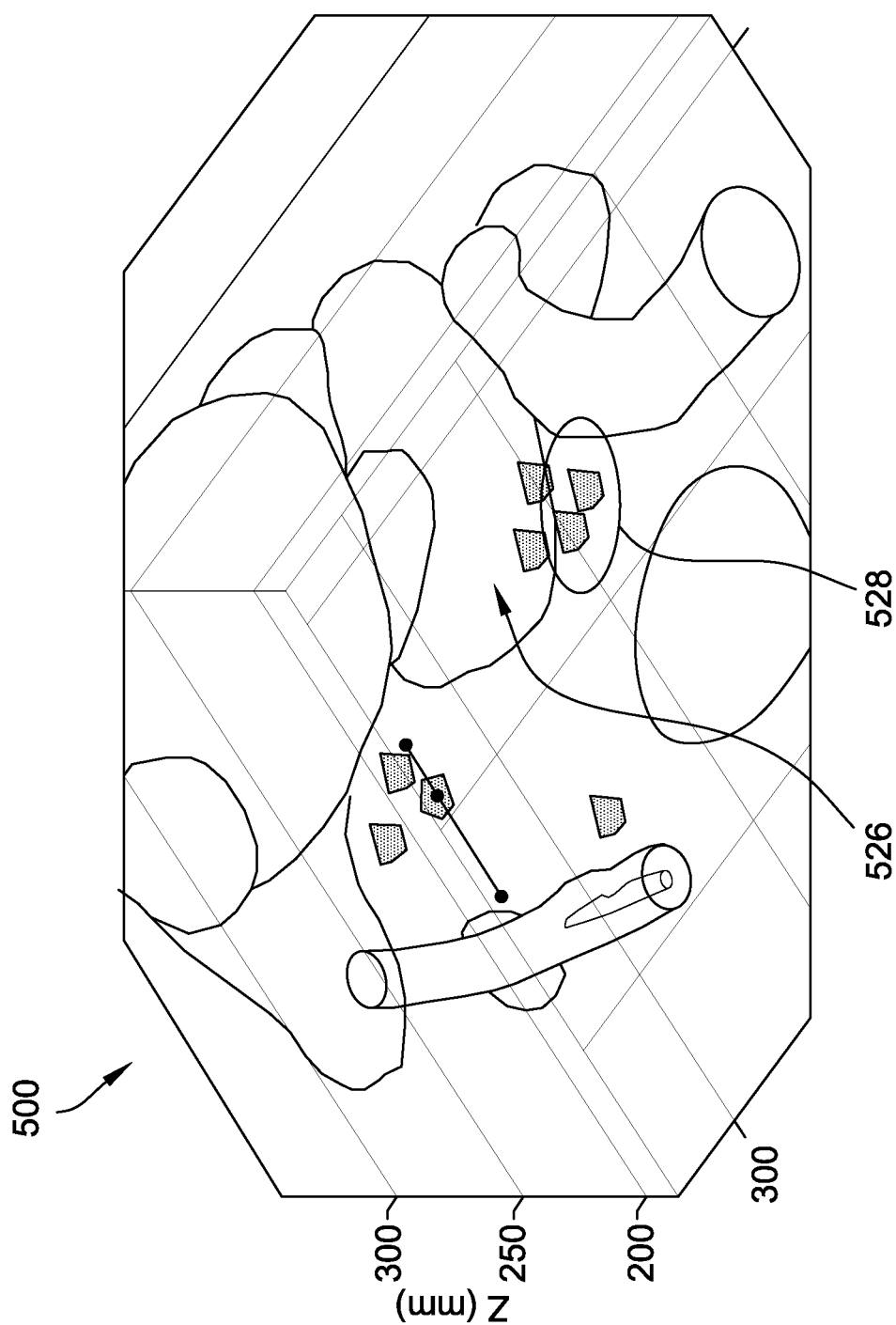
FIG. 7 is a detailed view of the patient model shown in FIG. 5 including the stomach and a group of tumors beneath.
Figure 8:
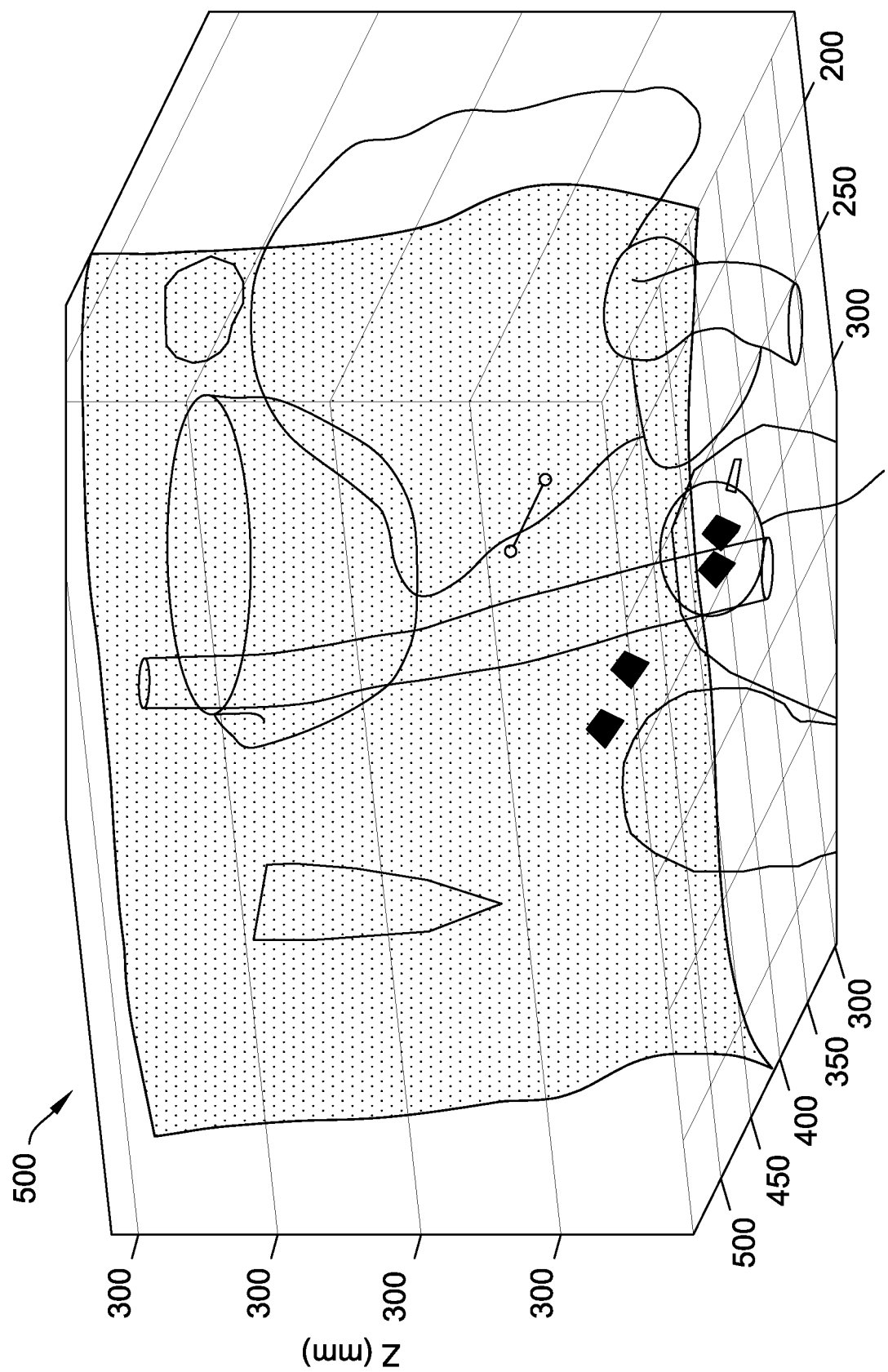
FIG. 8 is a detailed view of the small bowel structure within the patient model shown in FIG. 5 and a group of tumors.

FIGS. 5-10 are various views of an example patient model 500 reconstructed from a CT scan. FIG. 5 is an overview of the patient model 500 and ten tumors 502, 504, 506, 508, 510, 512, 514, 516, 518, 520 located in the abdomen of the patient. Notably, tumor 510 is located away from most OARs. Conversely, tumor 504 is located on or adjacent to the right kidney 522. FIG. 6 is a detailed view of the liver 524 and a group of tumors 528 collected beneath, including tumors 502, 508, and 514. FIG. 7 is a detailed view including the stomach 526 and a group of tumors 530 beneath, including tumors 506 and 516. FIG. 8 is a detailed view of the small bowel structure and a group of tumors 532, including tumors 512 and 520.

Figure 9:
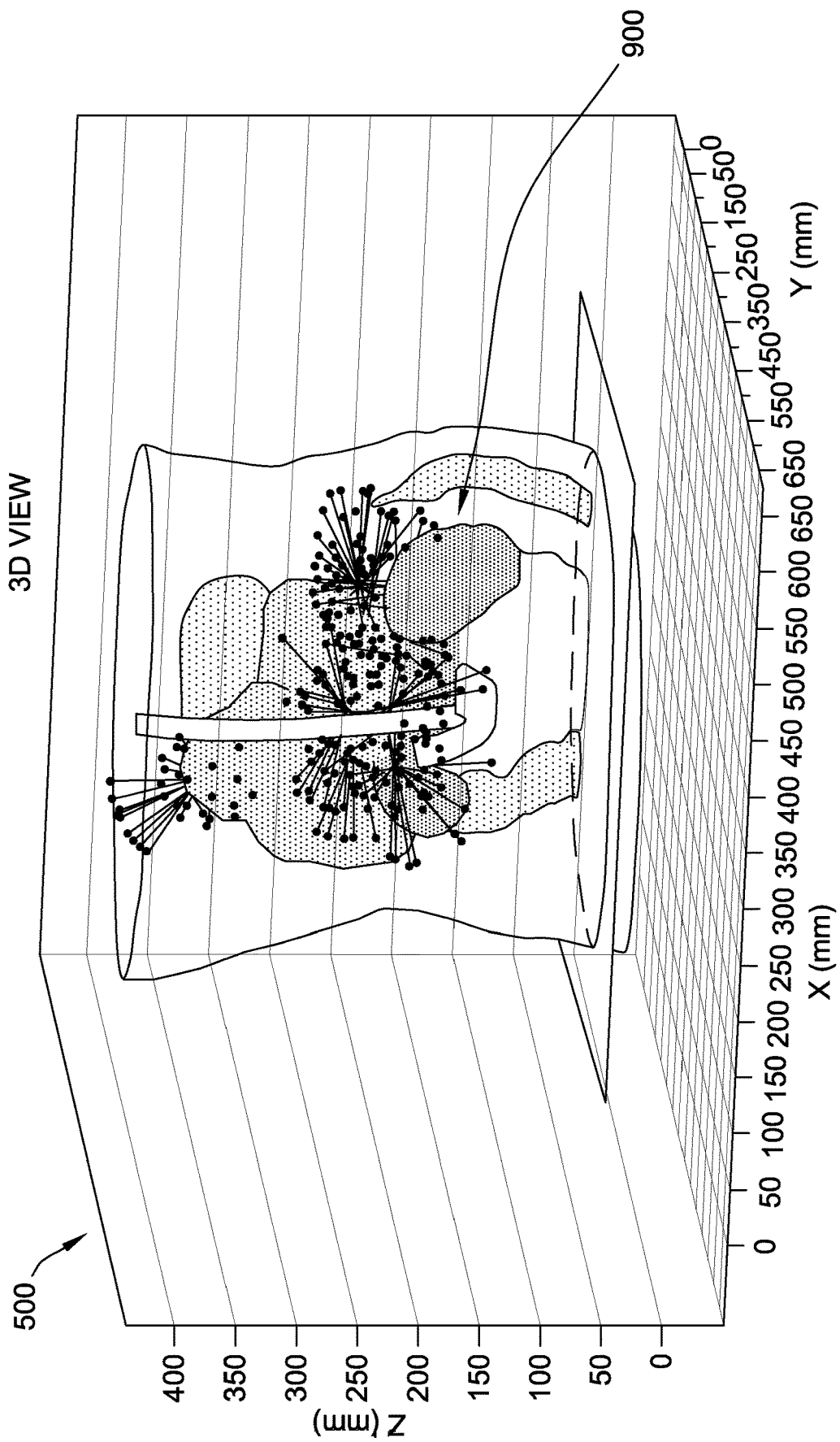
FIG. 9 is an illustration of an initial candidate beam set shown on the patient model of FIG. 5.

FIG. 9 is an illustration of an initial candidate beam set 900 shown on the patient model 500 based on initial conditions, i.e., prescribed dosage for each tumor and maximum dosage for each OAR, shown below in Table 3.

TABLE 3

Organ and Target Initial Conditions

| | ORGAN | | | | | | |
|---|---|---|---|---|---|---|---|
| | Kidney_R | Stomach | SmallBowel | LargeBowel | Liver | Heart | SpinalCord |
| Size | 6879 | 24150 | 70718 | 45347 | 95773 | 33117 | 1038 |
| Threshold Dose | 25 | 25 | 25 | 25 | 25 | 25 | 25 |

| | TARGET | | | | | | | | | |
|---|---|---|---|---|---|---|---|---|---|---|
| | 502 | 504 | 506 | 508 | 510 | 512 | 514 | 516 | 518 | 520 |
| Size | 125 | 125 | 343 | 137 | 137 | 137 | 137 | 137 | 137 | 137 |
| Need | 60 | 50 | 45 | 60 | 45 | 80 | 75 | 30 | 25 | 75 |

Figure 10:
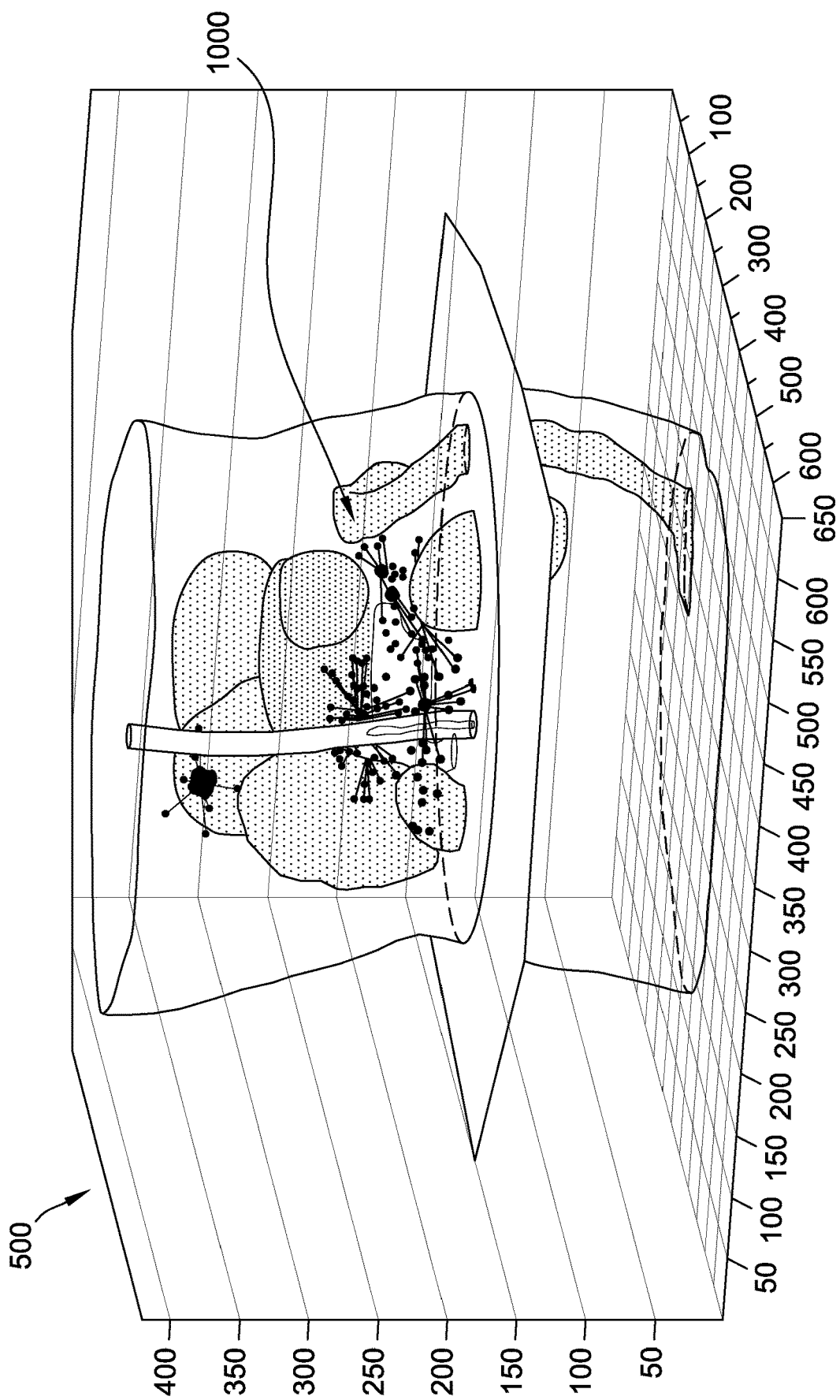
FIG. 10 is an illustration of a treatment beam set shown on the patient model of FIG. 5 and selected from the candidate beam set shown in FIG. 9.

FIG. 10 is an illustration of the treatment beam set 1000 shown on the patient model 500 selected according to the systems and methods described herein. More specifically, each candidate beam is scored for its effect on each organ and on each tumor by computing a weighted score based on the dosage provided by that beam and a priority value for either treating a given tumor or for minimizing dosage to a given OAR. The weighted scores are combined as a ratio of the organ score to the tumor score, such that a lower score is preferred for a given beam. Table 4 below shows pseudo code for the corresponding scoring function.

TABLE 4

| PSEUDO CODE FOR ORGAN SCORING | PSEUDO CODE FOR TUMOR SCORING |
|---|---|
| Each beam i is scored for each organ k: threshold[k] = sum of thresholds for all voxels in k dose[i][k] = sum of dose given by beam i to all voxels in k weight[k] = penalty weight of overdosage for organ k if dose [i] [k] > threshold [k] : score [i] [k] = ((dose [i] [k] − threshold [k])$^2$ + dose [i] [k] ) *weight [k] else: score [i] [k] = dose [i] [k] *weight[k] organScore [i] = sum of score [i] [k] for all k | Similarly for each tumor j: need[j] = sum of dosage need for all voxels in j dose [i] [j] = sum of dose given by beam i to all voxels in j weight[j] = weight of importance to meet dosage requirement for tumor j if dose [i] [j] > need [j] : score [i] [j] = need [j]$^{2}$*weight [j] else: score [i] [j] = dose [i] [j]$^{2}$*weight [j] tumorScore [i] = sum of score [i] [j] for all j |

The treatment beam set provides dosages set out in Table 5 below.

TABLE 5

Dosage summary for initial run

| | OARGAN | | | | | | |
|---|---|---|---|---|---|---|---|
| | Kidney_R | Stomach | SmallBowel | LargeBowel | Liver | Heart | SpinalCord |
| Size | 6879 | 24150 | 70718 | 45347 | 95773 | 33117 | 1038 |
| Threshold Dose | 25 | 25 | 25 | 25 | 25 | 25 | 25 |
| Average Dose | 6.0305 | 3.4332 | 2.7403 | 3.1366 | 3.0957 | 0.3767 | 5.2036 |
| Maximum Dose | 57.7865 | 23.5751 | 101.4885 | 30.4742 | 45.9117 | 7.5494 | 20.6825 |
| Average Dose Overflow | 12.1818 | 0 | 20.5384 | 2.7407 | 5.8480 | 0 | 0 |
| Overdosed Portion | 0.0750 | 0 | 0.0335 | 0.0011 | 0.0025 | 0 | 0 |
| Overdosed Size | 516 | 0 | 2366 | 52 | 240 | 0 | 0 |

| | TARGET | | | | | | | | |
|---|---|---|---|---|---|---|---|---|---|
| | 502 | 504 | 506 | 508 | 510 | 512 | 514 | 516 | 518 | 520 |
| Size | 125 | 125 | 343 | 137 | 137 | 137 | 137 | 137 | 137 | 137 |
| Dose | 63.5299 | 51.3902 | 45.1510 | 61.8268 | 47.4710 | 80.5458 | 75.7757 | 40.0457 | 42.2817 | 76.1925 |
| Need | 60 | 50 | 45 | 60 | 45 | 80 | 75 | 30 | 25 | 75 |

Embodiments of the systems and methods described herein enable a user, or physician, to quickly re-compute a treatment beam set based on changes to the prescribed dosage for each tumor or the maximum dosage for each OAR. For example, a physician may recognize, based on Table 5 above, that the small bowel would receive a significant overdose given the original treatment plan. Accordingly, the physician may reduce the prescribed dosage for tumors 512 and 520, because those are positioned nearest to the small bowel. An example treatment plan resulting from such a change provides dosages set out in Table 6 below.

TABLE 6

Changing Doses

| | OARGAN | | | | | | |
|---|---|---|---|---|---|---|---|
| | Kidney_R | Stomach | SmallBowel | LargeBowel | Liver | Heart | SpinalCord |
| Size | 6879 | 24150 | 70718 | 45347 | 95773 | 33117 | 1038 |
| Threshold Dose | 25 | 25 | 25 | 25 | 25 | 25 | 25 |
| Average Dose | 5.8272 | 1.8126 | 0.4055 | 2.1135 | 2.9457 | 0.4068 | 4.0178 |
| Maximum Dose | 56.5753 | 18.0556 | 14.5651 | 26.0060 | 45.7782 | 7.5494 | 16.8678 |
| Average Dose Overflow | 12.1330 | 0 | 0 | 0.5340 | 5.5259 | 0 | 0 |
| Overdosed Portion | 0.0737 | 0 | 0 | 0.00004 | 0.0027 | 0 | 0 |
| Overdosed Size | 507 | 0 | 0 | 2 | 259 | 0 | 0 |

TABLE 6-continued

| | Changing Doses | | | | | | | | |
|---|---|---|---|---|---|---|---|---|---|
| | TARGET | | | | | | | | |
| | 502 | 504 | 506 | 508 | 510 | 512 | 514 | 516 | 518 | 520 |
| Size | 125 | 125 | 343 | 137 | 137 | 137 | 137 | 137 | 137 | 137 |
| Dose | 62.5888 | 50.1224 | 45.1510 | 61.0133 | 46.1390 | 11.2570 | 75.6866 | 36.7122 | 37.1693 | 10.0718 |
| Need | 60 | 50 | 45 | 60 | 45 | 10 | 75 | 30 | 25 | 10 |

Notably, in Table 6, the physician's changes in dosage for tumors 512 and 520 resulted in significant reductions in overdosing the small bowel. Likewise, in certain embodiments, the systems and methods may be configured to create a hard restraint on overdosing one or more OARs. Accordingly, the overall dosing delivered to the tumors is affected, but overdosing for those OARs is restrained. Table 7 below illustrates a treatment plan for which a zero-overdose constraint is placed on the right kidney.

TABLE 7

| | No Overdose Restraints | | | | | | |
|---|---|---|---|---|---|---|---|
| | OARGAN | | | | | | |
| | Kidney_R | Stomach | SmallBowel | LargeBowel | Liver | Heart | SpinalCord |
| Size | 6879 | 24150 | 70718 | 45347 | 95773 | 33117 | 1038 |
| Threshold Dose | 25 | 25 | 25 | 25 | 25 | 25 | 25 |
| Average Dose | 4.5342 | 3.9002 | 4.2953 | 4.2810 | 5.8359 | 1.4513 | 9.3716 |
| Maximum Dose | 24.9995 | 23.5739 | 115.0184 | 30.7747 | 77.0693 | 18.2339 | 39.9528 |
| Average Dose Overflow | 0 | 0 | 22.6444 | 1.2064 | 7.5818 | 0 | 4.3856 |
| Overdosed Portion | 0 | 0 | 0.0403 | 0.0029 | 0.0180 | 0 | 0.0588 |
| Overdosed Size | 0 | 0 | 2851 | 130 | 1722 | 0 | 61 |

| | TARGET | | | | | | | | |
|---|---|---|---|---|---|---|---|---|---|
| | 502 | 504 | 506 | 508 | 510 | 512 | 514 | 516 | 518 | 520 |
| Size | 125 | 125 | 343 | 137 | 137 | 137 | 137 | 137 | 137 | 137 |
| Dose | 110.1327 | 22.1154 | 53.6531 | 73.7796 | 59.3678 | 94.0153 | 122.5723 | 46.9311 | 74.6795 | 83.4203 |
| Need | 60 | 50 | 45 | 60 | 45 | 80 | 75 | 30 | 25 | 75 |

Notably, no overdose is delivered to the right kidney. However, tumor 504, which is located on or adjacent to the right kidney, receives only a portion of the prescribed dosage under this treatment plan.

In certain embodiments, the systems and methods described herein provide an option to plan the treatment by omitting one tumor at a time from the plan. Table 8 below illustrates pseudo code for implementing such functionality, including the iterative removal and scoring of the candidate beams. Table 9 below illustrates the results of this procedure.

TABLE 8

| PSEUDO CODE FOR ORGAN SCORING | PSEUDO CODE FOR TUMOR SCORING |
|---|---|
| For each organ k: | For each tumor j: |
| threshold[k] = threshold dosage for organ k | need[j] = dosage need for tumor j |
| scorek = 0 | scorej = 0 |
| //score of organ k | //score of tumor j |
| for each voxel x in k: | for each voxel x in j: |
| if dose [x] > threshold [k] : | if dose [x] < need [j] : |
| scorek += sum( \| dose [x] − threshold [k] \| ) | score j += sum( \| dose [x] − need [j] \| ) |

TABLE 9

Subtracting one tumor at a time

| | Scores | | | | | | | | | | |
|---|---|---|---|---|---|---|---|---|---|---|---|
| | All Tumors | W/o 502 | W/o 504 | W/o 506 | W/o 508 | W/o 510 | W/o 512 | W/o 514 | W/o 516 | W/o 518 | W/o 520 |
| Kidney_R | 1.2e4 | 1.3e4 | 0 | 1.2e4 | 1.2e4 | 1.2e4 | 1.3e4 | 1.7e4 | 1.2e4 | 1.3e4 | 1.4e4 |
| Stomach | 0 | 382 | 390 | 0 | 0 | 410 | 0 | 0 | 0 | 0 | 0 |
| SmallBowel | 9.7e4 | 9.5e4 | 9.8e4 | 9.7e4 | 9.8e4 | 1.0e5 | 6.4e4 | 9.8e4 | 9.8e4 | 9.7e4 | 5.7e4 |
| LargeBowel | 285 | 139 | 42 | 278 | 282 | 310 | 8.89 | 204 | 209 | 285 | 3.64 |
| Liver | 2.8e3 | 2.8e3 | 3.1e3 | 2.6e3 | 1.8e3 | 2.7e3 | 2.9e3 | 2.4e3 | 2.8e3 | 2.9e3 | 3.1e3 |
| Heart | 0 | 0 | 0 | 0 | 0 | 0 | 0 | 0 | 0 | 0 | 0 |
| SpinalCord | 0 | 0 | 0 | 0 | 0.48 | 0 | 0 | 0 | 0 | 0 | 0 |
| 502 | 195 | 0 | 75.7 | 115 | 11.3 | 154 | 261 | 263 | 118 | 150 | 164 |
| 504 | 255 | 334 | 0 | 252 | 190 | 300 | 360 | 34.9 | 326 | 181 | 201 |
| 506 | 584 | 580 | 577 | 0 | 576 | 584 | 584 | 584 | 584 | 584 | 584 |
| 508 | 575 | 346 | 570 | 706 | 0 | 592 | 749 | 272 | 703 | 580 | 428 |
| 510 | 107 | 23.3 | 40.5 | 61.5 | 148 | 0 | 91.7 | 70.4 | 26.4 | 111 | 3.03 |
| 512 | 934 | 985 | 1.1e3 | 935 | 971 | 1.1e3 | 0 | 995 | 898 | 934 | 253 |
| 514 | 857 | 695 | 978 | 959 | 615 | 882 | 792 | 0 | 972 | 944 | 948 |
| 516 | 17.7 | 8.29 | 60.9 | 62.7 | 93.1 | 53.2 | 52.5 | 92.8 | 0 | 18.9 | 15.1 |
| 518 | 0 | 0 | 0 | 0 | 0 | 0 | 0 | 0 | 0 | 0 | 0 |
| 520 | 826 | 1.0e3 | 789 | 831 | 801 | 469 | 288 | 819 | 878 | 826 | 0 |

The results shown in Table 9 enable the physician to confirm patterns in treating certain tumors and the effect of such treatment on OARs and other tumors under the treatment plan. For example, Table 9 illustrates that inclusion of tumor 504 greatly affects the dosage delivered to the right kidney. Likewise, the small bowel benefits from a reduction in dosage delivered to tumors 512 and 520. Conversely, according to Table 9, a physician would recognize that tumor 518 can be effectively treated under all treatment plans.

Example technical effects of the methods, systems, and apparatus described herein include at least one of: (a) automating planning of radiotherapy for multiple tumors to minimize dosage to OARs and to provide prescribed dosage to the multiple tumors; (b) enabling physicians to customize an initial candidate beam set from which the treatment beams are selected; (c) enabling physicians to customize scoring of candidate beams; and (d) providing an seeding set of treatment beams that can be further optimized using traditional optimization algorithms.

Some embodiments involve the use of one or more electronic processing or computing devices. As used herein, the terms "processor" and "computer" and related terms, e.g., "processing device," "computing device," and "controller" are not limited to just those integrated circuits referred to in the art as a computer, but broadly refers to a processor, a processing device, a controller, a general purpose central processing unit (CPU), a graphics processing unit (GPU), a microcontroller, a microcomputer, a programmable logic controller (PLC), a reduced instruction set computer (RISC) processor, a field programmable gate array (FPGA), a digital signal processing (DSP) device, an application specific integrated circuit (ASIC), and other programmable circuits or processing devices capable of executing the functions described herein, and these terms are used interchangeably herein. The above embodiments are examples only, and thus are not intended to limit in any way the definition or meaning of the terms processor, processing device, and related terms.

In the embodiments described herein, memory may include, but is not limited to, a non-transitory computer-readable medium, such as flash memory, a random access memory (RAM), read-only memory (ROM), erasable programmable read-only memory (EPROM), electrically erasable programmable read-only memory (EEPROM), and non-volatile RAM (NVRAM). As used herein, the term "non-transitory computer-readable media" is intended to be representative of any tangible, computer-readable media, including, without limitation, non-transitory computer storage devices, including, without limitation, volatile and non-volatile media, and removable and non-removable media such as a firmware, physical and virtual storage, CD-ROMs, DVDs, and any other digital source such as a network or the Internet, as well as yet to be developed digital means, with the sole exception being a transitory, propagating signal. Alternatively, a floppy disk, a compact disc—read only memory (CD-ROM), a magneto-optical disk (MOD), a digital versatile disc (DVD), or any other computer-based device implemented in any method or technology for short-term and long-term storage of information, such as, computer-readable instructions, data structures, program modules and sub-modules, or other data may also be used. Therefore, the methods described herein may be encoded as executable instructions, e.g., "software" and "firmware," embodied in a non-transitory computer-readable medium. Further, as used herein, the terms "software" and "firmware" are interchangeable, and include any computer program stored in memory for execution by personal computers, workstations, clients and servers. Such instructions, when executed by a processor, cause the processor to perform at least a portion of the methods described herein.

Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

The systems and methods described herein are not limited to the specific embodiments described herein, but rather, components of the systems and/or steps of the methods may be utilized independently and separately from other components and/or steps described herein.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

As used herein, an element or step recited in the singular and proceeded with the word "a" or "an" should be understood as not excluding plural elements or steps unless such exclusion is explicitly recited. Furthermore, references to "one embodiment" of the present disclosure or "an example embodiment" are not intended to be interpreted as excluding the existence of additional embodiments that also incorporate the recited features.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of radiating a plurality of masses in a patient, the method comprising:
   receiving a three-dimensional model of the patient, the three-dimensional model including respective locations of a plurality of organs at risk;
   receiving a set of locations in the three-dimensional model corresponding to the plurality of masses;
   receiving respective prescribed radiation dosages for the plurality of masses;
   receiving respective radiation limits for the plurality of organs at risk;
   computing a candidate set of beams having respective beam paths that travel through at least one of the plurality of masses;
   scoring the candidate set of beams based on respective dosages provided to the plurality of masses, respective dosages provided to the plurality of organs at risk, and beams in a set of selected beams for treatment, wherein scoring the candidate set of beams comprises:
      improving a score of a candidate beam according to a first dosage provided by the candidate beam to the plurality of masses; and
      penalizing the score of the candidate beam according to a second dosage provided by the candidate beam to at least one of the plurality of organs at risk;
   adding a best-scoring beam among the candidate set of beams to the set of selected beams; and
   radiating the plurality of masses using the set of selected beams.

2. The method of claim 1, wherein computing the candidate set of beams comprises, for each pair of masses in the plurality of masses:
   extending a plurality of beam paths from a first mass; and
   identifying candidate beam paths that extend through a second mass.

3. The method of claim 1, wherein computing the candidate set of beams comprises, for each mass in the plurality of masses:
   extending respective beam paths from a plurality of sample locations on the skin of the patient through the mass.

4. The method of claim 1, wherein computing the candidate set of beams comprises limiting the candidate set of beams to a quantity selected by a user.

5. The method of claim 1, wherein scoring the candidate set of beams comprises, for each beam of the candidate set of beams:
   computing respective dosage scores for each mass of the plurality of masses according to respective dosages provided to each mass; and
   summing the respective dosage scores to an aggregate dosage score.

6. The method of claim 5, wherein computing the respective dosage scores comprises scaling the respective dosages provided to each mass by a respective fraction of the respective prescribed radiation dosage that each beam provides.

7. The method of claim 5, wherein scoring the candidate set of beams comprises, for each beam of the candidate set of beams:
   computing respective penalties for each organ of the plurality of organs at risk according to respective dosages provided to each organ;
   summing the respective penalties to an aggregate penalty; and
   subtracting the aggregate penalty from the aggregate dosage score, yielding the score for the beam.

8. The method of claim 7, wherein computing the respective penalties comprises scaling the respective dosages provided to each organ by a respective fraction of the respective radiation limit that each beam provides.

9. The method of claim 1, wherein scoring the candidate set of beams comprises penalizing the score of a candidate beam according to a dosage provided to a one of the plurality of masses by the set of selected beams.

10. The method of claim 9, wherein penalizing the score of the candidate beam comprises scaling the score by a complement of a fraction of the respective prescribed radiation dosage for the one of the plurality of masses provided by the set of selected beams.

11. The method of claim 1 further comprising:
    re-scoring the candidate set of beams based on respective dosages provided to the plurality of masses, respective dosages provided to the plurality of organs at risk, and beams in the set of selected beams for treatment; and
    adding a next highest-scoring beam among the candidate set of beams to the set of selected beams.

12. The method of claim 11 further comprising repeating the re-scoring and the adding until an ending condition is met for the set of selected beams, the ending condition selected from the group consisting of:
    the respective prescribed radiation dosages for at least one of the plurality of masses is met,
    the respective prescribed radiation dosages for all of the plurality of masses is met, and
    a threshold number of candidate beams have been added to the set of selected beams.

13. The method of claim 1, wherein scoring the candidate set of beams further comprises:
    for each beam in the candidate set of beams,
       determining a score of tumor voxels for the each beam by:
          for each tumor voxel j in tumor voxels, determining a score of the each beam at the each tumor voxel j; and
          combining the score of the each beam at the each tumor voxel for all tumor voxels;

determining a score of organ voxels for the each beam by:
for each organ voxel k in organ voxels, determining a score of the each beam at the each organ voxel k; and
combining the score of the each beam at the each organ voxel for all organ voxels; and
determining a score of the each beam as a difference between the score of tumor voxels and the score of organ voxels.

14. A system for administering radiation therapy for a plurality of masses in a patient, the system comprising:
a radiation therapy beam generator;
an interface configured to receive:
a three-dimensional model of the patient, the three-dimensional model including respective locations of a plurality of organs at risk;
a set of locations in the three-dimensional model corresponding to the plurality of masses;
respective prescribed radiation dosages for the plurality of masses; and
respective radiation limits for the plurality of organs at risk; and
a processing system coupled to the interface and the radiation therapy beam generator, the processing system configured to:
compute a candidate set of beams having respective beam paths that travel through at least one of the plurality of masses;
score the candidate set of beams based on respective dosages provided to the plurality of masses, respective dosages provided to the plurality of organs at risk, and beams in a set of selected beams for treatment by:
improving a score of a candidate beam according to a first dosage provided by the candidate beam to the plurality of masses; and
penalizing the score of the candidate beam according to a second dosage provided by the candidate beam to at least one of the plurality of organs at risk;
add a best-scoring beam among the candidate set of beams to the set of selected beams;
transmit the set of selected beams to the radiation therapy beam generator; and
initiate generation of the set of selected beams by the radiation therapy beam generator.

15. The system of claim 14, wherein the processing system is further configured to compute the candidate set of beams by, for each pair of masses in the plurality of masses:
extending a plurality of beam paths from a first mass; and
identifying candidate beam paths that extend through a second mass.

16. The system of claim 14, wherein the processing system is further configured to compute the candidate set of beams by, for each mass in the plurality of masses:
extending respective beam paths from a plurality of sample locations on the skin of the patient through the mass.

17. The system of claim 14, wherein the processing system is further configured to limit the candidate set of beams to a quantity selected by a user.

18. The system of claim 14, wherein the processing system is further configured to score the candidate set of beams, for each beam of the candidate set of beams, by:
computing respective dosage scores for each mass of the plurality of masses according to respective dosages provided to each mass; and
summing the respective dosage scores to an aggregate dosage score.

19. The system of claim 18, wherein the processing system is further configured to score the candidate set of beams, for each beam of the candidate set of beams, by:
computing respective penalties for each organ of the plurality of organs at risk according to respective dosages provided to each organ;
summing the respective penalties to an aggregate penalty; and
subtracting the aggregate penalty from the aggregate dosage score, yielding the score for the beam.

20. The system of claim 18, wherein the processing system is further configured to:
remove one mass from the plurality of masses;
re-score the candidate set of beams for the plurality of masses; and
repeat the removal and the rescoring for each mass of the plurality of masses.

21. The system of claim 14, wherein the processing system is further configured to score the candidate set of beams by penalizing the score of a candidate beam according to a dosage provided to a one of the plurality of masses by the set of selected beams.

22. The system of claim 21, wherein the processing system is further configured to penalize the score of the candidate beam by scaling the score by a complement of a fraction of the respective prescribed radiation dosage for the one of the plurality of masses provided by the set of selected beams.

23. The method of claim 13, wherein:
determining the score of the each beam i at the each tumor voxel j as:

$$scoreT[i][j] = \frac{dose[i][j]}{dt[j]} * \min\left(1 - \frac{received[j]}{dt[j]}, 0\right),$$

where score T[i][j] is the score of the each beam i at the each tumor voxel j, dt[j] is a prescribed dosage goal at the each tumor voxel j, dose[i][j] is a dosage imposed by the each beam i at the each tumor voxel j, and received[j] is a dosage already received by the each voxel j so far; and
determining the score of the each beam i at the each organ voxel k as:

$$scoreO[i][k] = \begin{cases} \frac{dose[i][k]}{do[k]}, & \text{if } received[k] < do[k] \\ \frac{dose[i][k]}{do[k]} * \left(\frac{received[k]}{do[k]}\right)^2, & \text{if } received[k] \geq do[k] \end{cases},$$

where score O[i][k] is the score of the each beam i at the each organ voxel k, do[k] is a specified dosage upper-bound goal at the each organ voxel k, dose[i][k] is a dosage imposed by the each beam i at the each organ voxel k, and received[k] is a dosage already received by the each organ voxel k so far.

* * * * *